(12) United States Patent
Davenport et al.

(10) Patent No.: US 6,723,565 B2
(45) Date of Patent: Apr. 20, 2004

(54) PULSED-FLOW TOTAL ORGANIC CARBON ANALYZER

(75) Inventors: Ronald J. Davenport, Superior, CO (US); Richard D. Godec, Longmont, CO (US)

(73) Assignee: Sievers Instruments, Inc., Boulder, CO (US)

( * ) Notice: Subject to any disclaimer, the term of this patent is extended or adjusted under 35 U.S.C. 154(b) by 0 days.

(21) Appl. No.: 10/333,435

(22) PCT Filed: Oct. 15, 2001

(86) PCT No.: PCT/US01/31991
§ 371 (c)(1),
(2), (4) Date: Jan. 21, 2003

(87) PCT Pub. No.: WO02/33401

PCT Pub. Date: Apr. 25, 2002

(65) Prior Publication Data

US 2003/0211626 A1 Nov. 13, 2003

Related U.S. Application Data

(60) Provisional application No. 60/240,701, filed on Oct. 16, 2000.

(51) Int. Cl.[7] .............................................. G01N 31/12
(52) U.S. Cl. .................... 436/133; 436/146; 422/82.02; 422/78; 422/90
(58) Field of Search ................................ 436/133, 146, 436/150, 159; 422/82.02, 78, 90

(56) References Cited

U.S. PATENT DOCUMENTS

| | | | |
|---|---|---|---|
| 4,868,127 A | | 9/1989 | Blades et al. |
| 5,272,091 A | | 12/1993 | Egozy et al. |
| 5,275,957 A | | 1/1994 | Blades et al. |
| 5,677,190 A | | 10/1997 | Melanson et al. |
| 5,750,073 A | | 5/1998 | Godec et al. |
| 5,798,271 A | | 8/1998 | Godec et al. |
| 6,319,723 B1 | * | 11/2001 | Jeffers et al. ............... 436/133 |
| 6,447,725 B1 | * | 9/2002 | Inoue et al. .................. 422/80 |
| 6,451,613 B1 | * | 9/2002 | Blades et al. ............... 436/146 |

* cited by examiner

Primary Examiner—Jeffrey R. Snay
(74) Attorney, Agent, or Firm—David Silverstein; Andover-IP-Law

(57) ABSTRACT

Methods and apparatus are disclosed for determination of the total concentration of organic carbon compounds in aqueous process streams utilizing a pulsed-flow technique for irradiating a water sample in a chamber (3) with UV or similar wavelength radiation.

29 Claims, 5 Drawing Sheets

FILTER, UV REACTOR, UV LIGHT, AND MEASUREMENT CELL

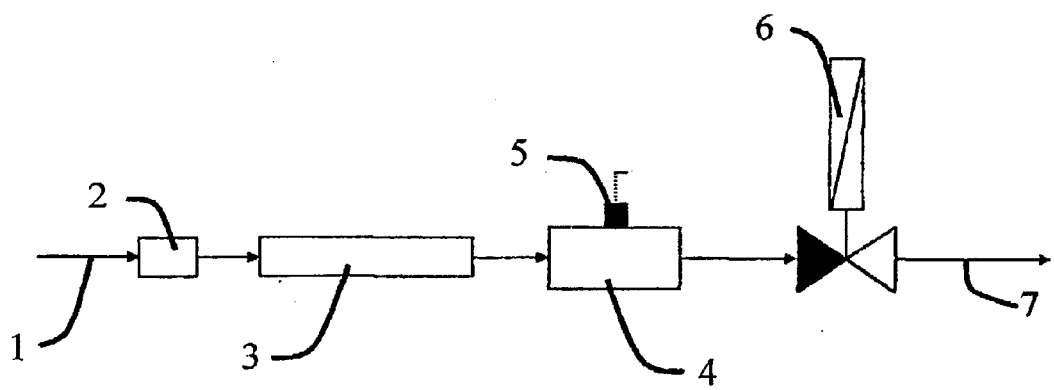
FIGURE 1   PULSED-FLOW TOC ANALYZER MECHANICAL COMPONENTS

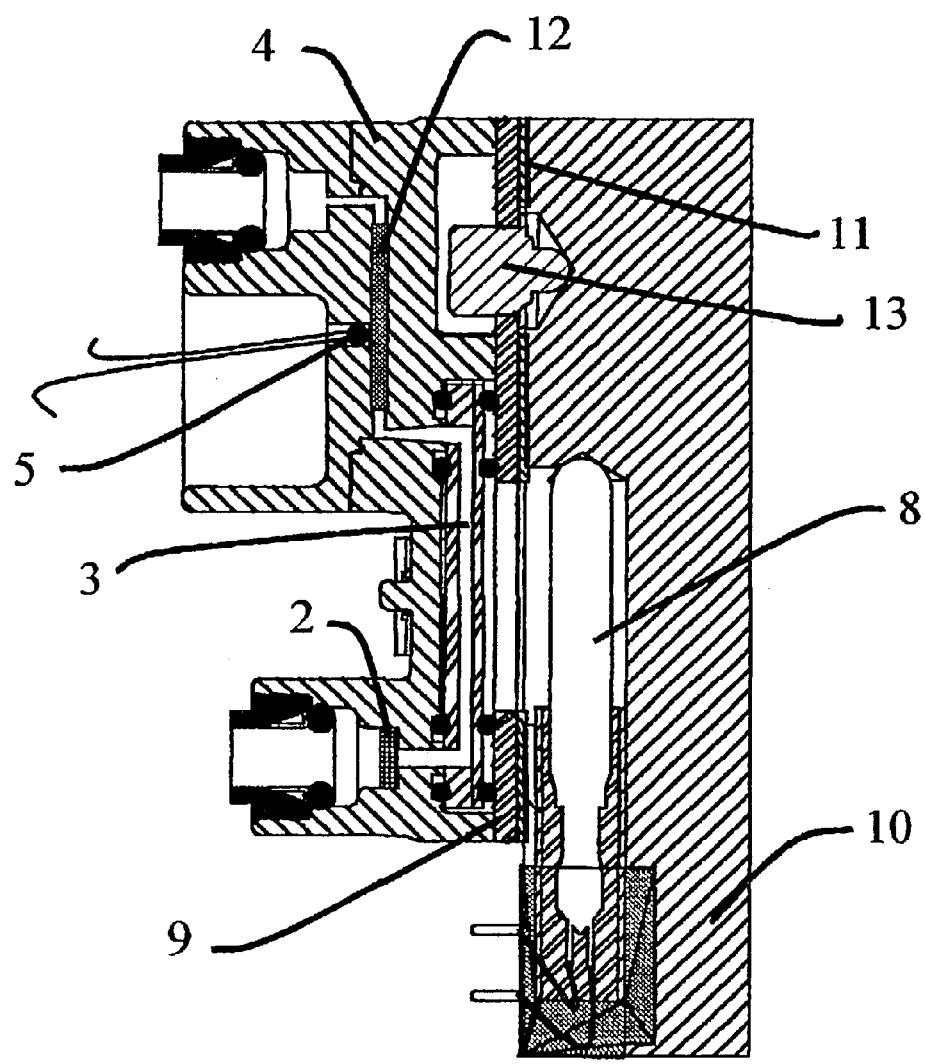
FIGURE 2 FILTER, UV REACTOR, UV LIGHT, AND MEASUREMENT CELL

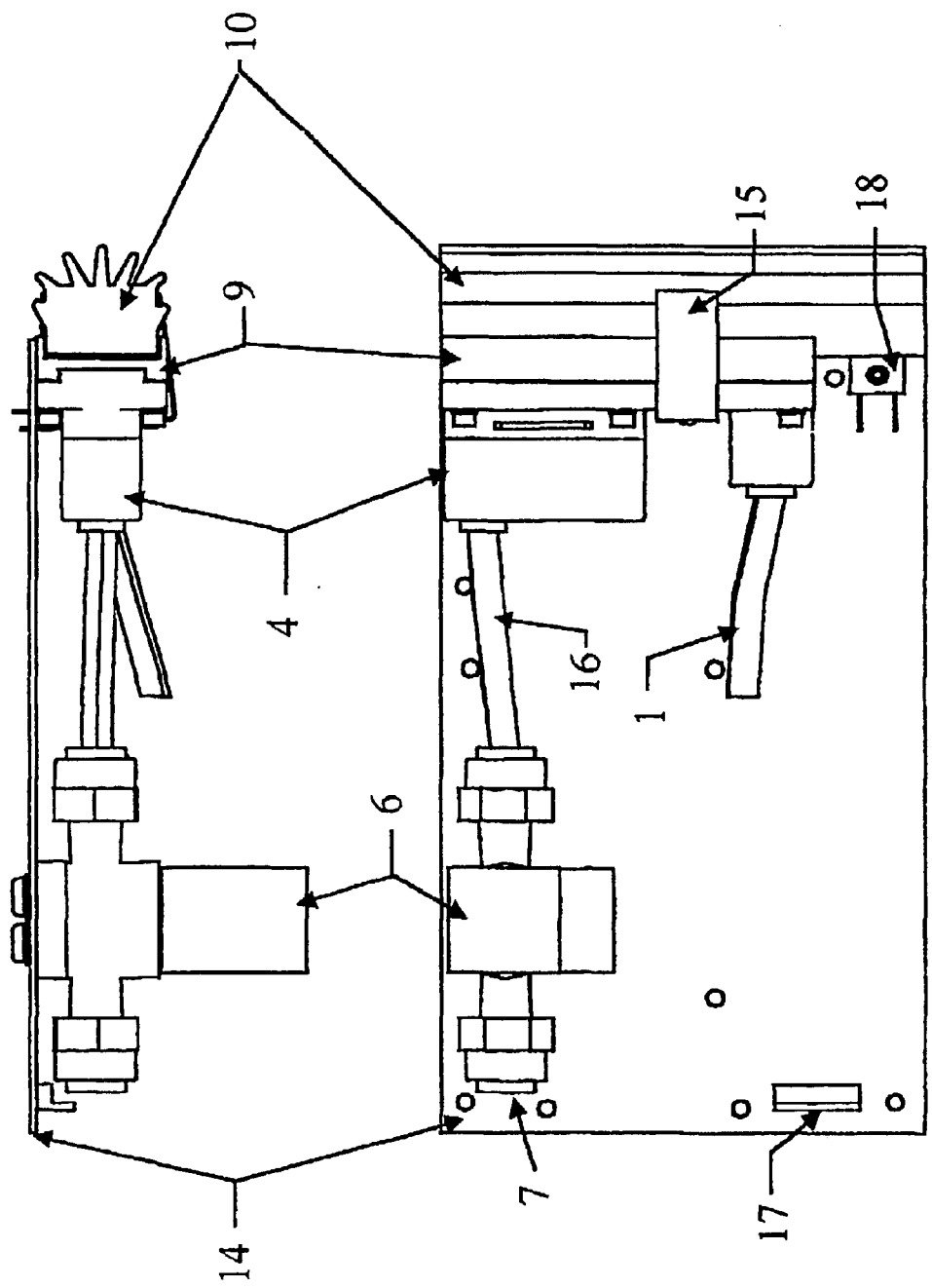
FIGURE 3 PULSED-FLOW TOC ANALYZER

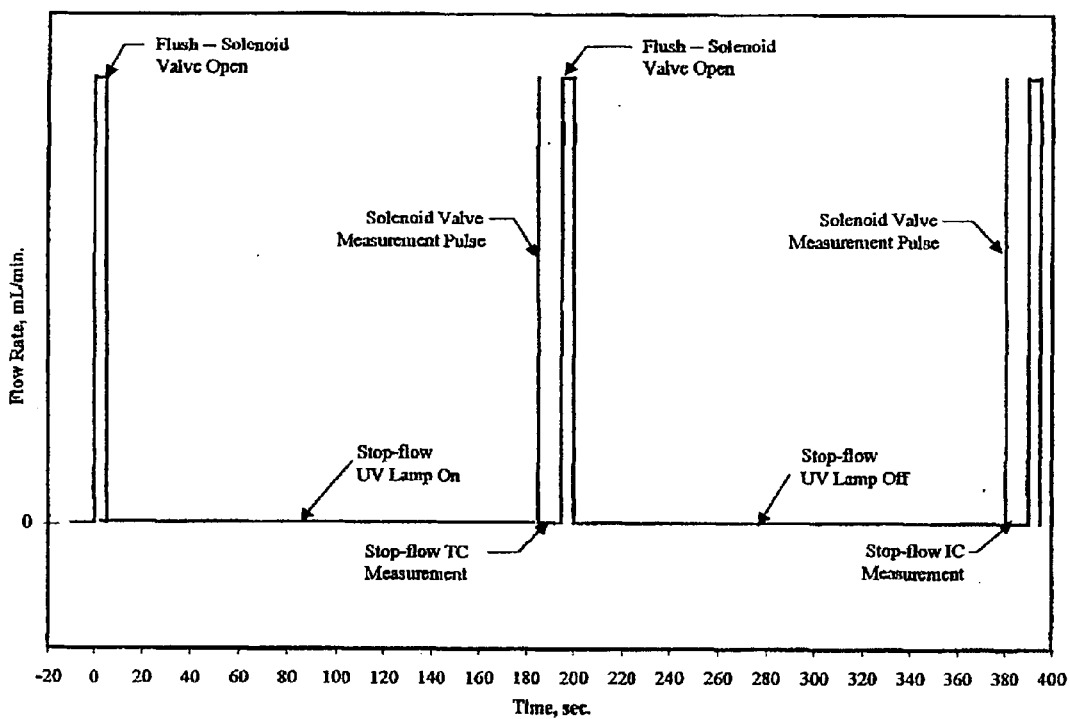
FIGURE 4  ANALYSIS SEQUENCE

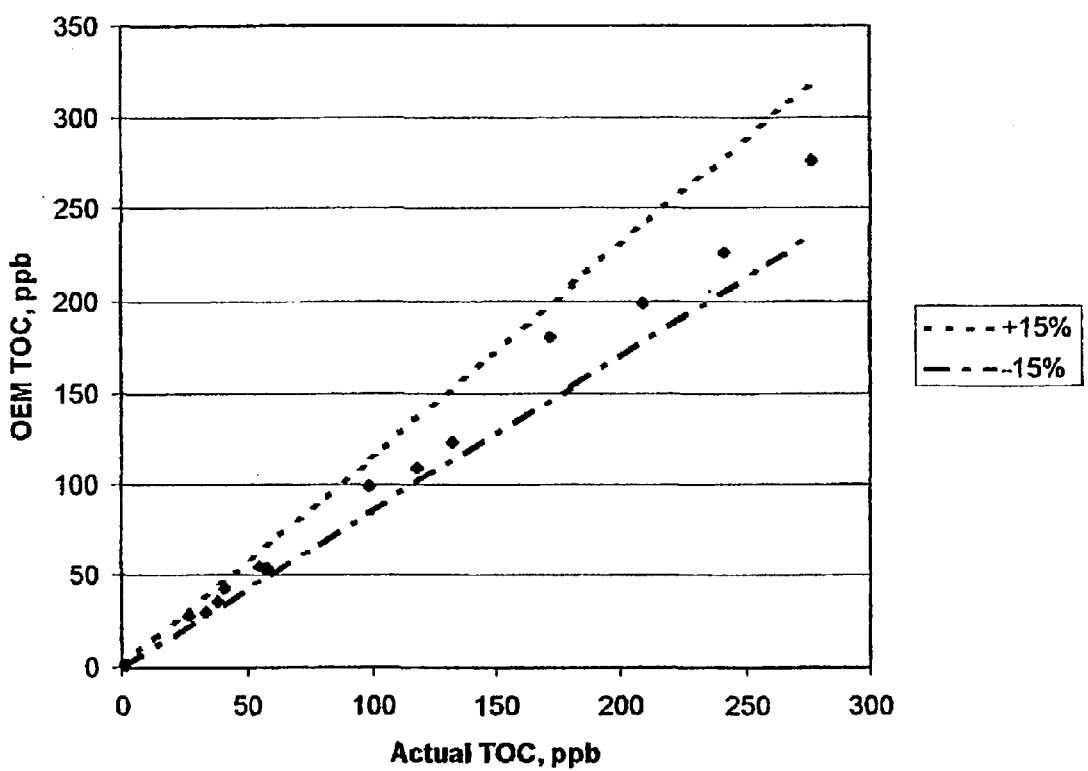
FIGURE 5 RESPONSE TO TOC

PULSED-FLOW TOTAL ORGANIC CARBON ANALYZER

This application claims the benefit of Provisional application Ser. No. 60/240,701, filed Oct. 16, 2000.

The present invention relates to improved methods and apparatus for determination of the total concentration of organic carbon compounds in aqueous process streams. The invention is especially adapted for use in measuring carbon in deionized water or deionized water with dissolved carbon dioxide, which is often used in research and development laboratories, and in manufacture and processing of electronic components, fine chemicals and pharmaceuticals.

Particularly, the method of the present invention in a preferred embodiment includes oxidation of organic components of a sample stream of water and measurement of electrical conductance and/or electrical resistance of such stream thereafter (preferably also the temperature of such stream). The preferred embodiment requires no pump or flow control components other than an on/off valve (e.g., a solenoid valve), making it inexpensive and reliable. Further, the cell containing the conductivity electrodes and temperature sensor is removable from other components of the sensor for maintenance or calibration when required.

BACKGROUND OF THE INVENTION

Measurement of Total Organic Carbon (TOC) is a well-established method of determining the concentration of organic contaminants in water [e.g., Van Hall, C. E.; Safranko, J. and Stenger, V. A., "Rapid Combustion Method for the Determination of Organic Substances in Aqueous Solutions," Anal. Chem., Vol. 35(3), pp. 315–319; 1963; also, Poirier, S. J. and Wood, J. H., "A New Approach to the Measurement of Organic Carbon," Am. Laboratory, pp. 1–7; December 1978.]. In all TOC measurement techniques, carbon in the organic contaminants is oxidized to carbon dioxide, which is measured by a variety of means.

Water may already contain carbon dioxide and other inorganic sources of carbon, so it is necessary to either eliminate Inorganic Carbon (IC) from the sample, or measure IC, prior to TOC measurement. In those techniques that measure IC, carbon dioxide concentration, after oxidation of the organics, is the sum of carbon dioxide from organic and inorganic sources—Total Carbon (TC). TOC concentration is calculated from the difference between TC and IC. (As used herein, "carbon dioxide" is intended to include free carbon dioxide, carbonic acid and bicarbonate.)

A variety of prior art approaches for measuring TOC content of water have been proposed. The so-called "differential conductivity" technique involves measurement of conductivity and temperature before and after the oxidation of the organic components of the water sample. Oxidation is initiated by action of ultraviolet (UV) light on the sample water.

The differential conductivity technique was implemented using either a continuously flowing sample stream [e.g., Bender, D. and Bevilacqua, A. C., "Portable Continuous TOC Monitoring in a Semiconductor Water System," Ultrapure Water, pp. 58–67; October 1999; see also U.S. Pat. No. 4,749,657] or a sample stream that operates in a stop-flow mode [e.g., Gallegos, P.; Stillian, J.; and Rasmussen, J., "Conductometrically Based TOC Detection Instrumentation's Accuracy in Semiconductor High-Purity Water," Proceedings of Watertech '99 Executive Forum, pp. P1–P21; Portland, Oreg.; Oct. 5–6,1999; see also U.S. Pat. Nos. 4,868,127; 5,275,957; and 5,677,190].

Problems with the Continuous-Flow Approach

The continuous-flow approach is usually used where fast detection of rapidly changing TOC concentrations is desired. At least two conductivity cells are usually used. Water flows continuously through a first conductivity cell, then the UV reactor, and finally the second conductivity cell. The difference in temperature-compensated conductivity measurements between the two cells is used to calculate the response of the analyzer.

The flow rate of water is necessarily rapid to achieve this rapid response. To be economically competitive, the UV reactors are made too small at those flow rates for the UV exposure to oxidize organics all the way to carbon dioxide. Instead, organic acids are formed, and these acids increase conductivity of water more than carbon dioxide does at the same concentration. This produces a large positive error in measurement of TOC. To overcome this problem, those analyzers must be calibrated with solutions that contain organic compounds thought to be similar to those in the unknown water sample. Since composition of all process waters actually changes with time, these analyzers do not accurately report TOC values.

A second problem with continuous-flow techniques is that they require the flow rate be held constant, even when water pressure changes. Otherwise, already quite inaccurate measurements become unusable. This necessitates addition of relatively expensive and complex flow- and pressure-control devices to those analyzers. The analyzers also require the operator to monitor flow rate of the sample, and to make periodic manual adjustments to the flow.

Problems with the Stop-Flow Approach

In the stop-flow approach, measurements are not affected by variations in water pressure, so flow- and pressure-control devices are not required. This is because conductivity electrodes are placed inside the UV reactor, allowing conductivity measurements to be made while water is stopped in the UV reactor. Only a solenoid valve or similar device is required to stop sample flow.

Conductivity and temperature of the water are measured, then flow is stopped, the UV lamp is turned on and oxidizes organics. When oxidation is thought to be complete, conductivity and temperature of the solution are measured again. TOC concentration is calculated from the difference in temperature-compensated conductivity measurements made before and after oxidation. Then the solenoid valve is opened to allow the UV reactor to be flushed out with a fresh water sample, in preparation for the next measurement.

A problem with the stop-flow approach stems from the fact that the electrodes are in the UV reactor. The UV lamp illuminates the electrodes during the oxidation period, and they generally are coated with a photocatalytic material, such as titanium dioxide. When illuminated, this material catalyzes oxidation of organics. The problem is that some organics are converted to organic acids and later are further oxidized to carbon dioxide. Such organic acids initially make the water more conductive than it will be later when the acids are converted to carbon dioxide. This means conductivity peaks at a very high level, and then decreases as acids are converted to carbon dioxide. Conductivity asymptotically approaches a steady-state value as all of the acids are converted to carbon dioxide. If conductivity is measured too soon, a positive error results in TOC measurement.

To avoid this mistake, some stop-flow TOC analyzers make repetitive conductivity and temperature measurements. Complex algorithms must be used to monitor temperature-compensated conductivity to detect conductivity peaks. When a peak is detected, the analyzer must track the subsequent decrease in conductivity to estimate its steady-state value. This requirement increases the time for the measurement, and makes it impossible to predict how long each measurement will require. Additionally, the algorithm increases the complexity of the analyzer and cost of its electronics.

A second problem is that, because the conductivity electrodes are placed inside the UV reactor, they cannot be removed easily for maintenance or calibration unless the UV reactor is constructed with multiple parts, including seals around the conductivity electrodes. This complexity makes the UV reactor larger, increases cost, and decreases reliability.

A third problem is that stop-flow TOC analyzers are subject to errors in the conductivity measurement used to calculate the IC concentration. Hydrogen peroxide is known to be formed by electrodes in contact with water containing dissolved oxygen, even in the absence of UV light [e.g., Clechet, P.; Martelet, C.; Martin, J. R. and Olier R., "Photoelectrochemical Behaviour of TiO2 and Formation of Hydrogen Peroxide," Electrochimica Acta, Vol. 24, pp. 457–461; 1979]. Hydrogen peroxide decomposes to oxygen by a reaction mechanism that is catalyzed by metals (i.e., conductivity electrodes). This catalyzed decomposition proceeds through formation of highly reactive hydroxyl radicals [e.g., Cotton, F. A. and Wilkinson, G., Advanced Inorganic Chemistry, Second Ed.; Interscience Publishers, New York, N.Y., pp. 374; 1966]. Hydroxyl radicals react with organics in the UV reactor before the UV lamp is turned on, forming acids and other species that produce highly conductive ions in solution. Thus, the IC conductivity measurement can have significant positive errors, which cause low errors in TOC concentration calculation.

A fourth problem exists. Even in the absence of reactions at the surface of the electrodes, described above, conductivity electrodes and other UV reactor materials leach ions into the water. These ions increase conductivity of water, and they cause errors in both IC and TC measurements.

A fifth problem is that, in the presence of UV light and dissolved oxygen in the water sample, the TOC measurement exhibits a positive error due to formation of hydrogen peroxide. Dissociation of hydrogen peroxide itself results in an increase in conductivity of water [Gallegos, P.; Stillian, J.; and Blades, R., "Light Dependent Compensation of TOC Measurement and its Relationship with Dissolved Oxygen Concentrations in Ultrapure Rinse Water for Semiconductor Manufacturing," presented at 18th Annual Semiconductor Pure Water and Chemicals Conference in Santa Clara, Calif.; Mar. 1–4, 1999.]

Other prior art approaches to measuring TOC content of water include U.S. Pat. Nos. 3,958,941 of Regan; 4,749,657 of Takahashi; 5,518,608 of Chubachi; 4,868,127 and 5,275,957 of Blades; 5,677,790 of Melanson; and 5,272,091 of Egozy.

In U.S. Pat. No. 3,958,941 of Regan, an aqueous sample is introduced into a circulating water stream that flows through a reaction chamber where the sample is mixed with air and exposed to UV radiation to promote oxidation of organic compounds found in the sample to form carbon dioxide. Free carbon dioxide formed in the reaction chamber is then removed from solution by an air stripping system and introduced into a second chamber containing water that has been purified to remove ionic compounds. Conductivity of water in the second chamber is measured, and any increase in conductivity is related to the total concentration of carbon dioxide following oxidation in the first reactor. The conductivity measurement can be used, therefore, to determine the concentration of total carbon in the original sample. If the concentration of inorganic carbon is known, or if inorganic carbon compounds are removed prior to the measurement, the concentration of organic carbon can be determined.

In U.S. Pat. No. 4,749,657 of Takahashi, sample flows continuously through a UV light reaction zone, in the presence of oxygen, and is partially oxidized (but not completely) to carbon dioxide. Conductivity of the partially oxidized organics is measured in a conductivity cell. An inlet conductivity cell also may be employed to determine the original conductivity of the solution.

In U.S. Pat. No. 5,518,608 of Chubachi, a plant for producing and using ultrapure water is described, consisting of a first TOC monitor, a water purifier containing ion exchange resins, and a second TOC monitor. TOC concentration in the purifier output water is continuously monitored to allow early detection of when the ion exchange resin is deteriorated. The "TOC monitors" referred to are identified as resistivity sensors elsewhere in the patent.

In U.S. Pat. Nos. 4,868,127 and 5,275,957 of Blades, a water sample is introduced into a sample cell, the body of which is constructed from Teflon or ceramic. The cell contains a quartz window, sealed with an O-ring. On the other side of the quartz window is a housing that contains a UV lamp. Two concentric circular electrodes are located inside the cell, and are constructed of titanium, palladium, iridium, rhodium or platinum. A temperature sensor is in contact with one of the electrodes. Temperature-compensated conductivity measurements are made before, during and after oxidation of organic compounds in the water sample. When oxidation is complete, the sample water is allowed to flush the cell out prior to the next measurement.

In U.S. Pat. No. 5,677,790 of Melanson, a measurement cell and circuitry are described. The cell is constructed from quartz or glass tubing, and a pair of wire electrodes is positioned longitudinally inside the cell. The electrodes are made from titanium and have catalytic titanium dioxide surfaces. A temperature sensor is mounted outside, but in contact with, the measurement cell wall. A UV lamp is positioned to irradiate the measurement cell and the electrodes inside it. The circuit used to monitor temperature-compensated conductivity of the solution in the measurement cell multiplexes a drive signal between the conductivity electrodes, a calibration resistor, and the temperature sensor.

In U.S. Pat. No. 5,272,091 of Egozy, water passes through a resistivity cell and a three-way valve. In one position, the three-way valve directs water into an oxidation zone (UV reactor) and a second resistivity cell. In the other position, the three-way valve bypasses flow of water away from the oxidation zone. This allows a portion of the water to remain stagnant in the oxidation zone for any desired time. When the three-way valve next directs flow into the oxidation zone, water that has remained there during the oxidation period now flows through the second resistivity cell. This allows the resistivity of the oxidized water to be measured for a variety of oxidation periods. Resistivity that would be measured after infinitely long oxidation periods can be estimated. That estimate is then used to calculate TOC concentration in the water.

Disadvantages of Former Methods

The Regan device is slow, cannot be used for continuous monitoring of TOC concentration in aqueous streams, cannot be scaled down without increasing interference from $NO_2$, $SO_2$, and $H_2S$ to unacceptable levels, and is generally unsatisfactory. In any system that requires removal of carbon dioxide from an aqueous solution by air stripping, pH of the solution must be reduced to 4.0 or less to ensure that all carbon is in the form of free carbon dioxide. The Regan patent does not teach that acid must be added to the sample stream to achieve this requirement.

In the method of Takahashi, UV light, in the presence of oxygen, only partially oxidizes organic compounds. Carbon dioxide is not produced as the end product of oxidation. The products of oxidation are indeterminate, and vary with time as the organic compounds in the influent water vary. Even when composition of influent water does not change, oxidation products change with water flow rate, temperature, and other operating parameters. This is because these parameters change the degree to which the original compounds in the water are oxidized. This produces inaccurate TOC measurements because conductivity of compounds produced in the oxidation differ from one another. In an attempt to control operating parameters, expensive flow- and pressure-control components must be added. The operator also must make adjustments to these devices periodically, which increases operating costs of the Takahashi method.

The Chubachi device has the same disadvantages as the Takahashi invention.

The Blades devices and the Melanson device have several disadvantages. In these devices, conductivity electrodes are located in the UV reactor and are covered with a photocatalyst. Because photocatalyzed reactions occur at the electrode surfaces, conductivity measurements are confounded by initial production of organic acids. These acids are produced before some organics are completely oxidized to carbon dioxide. The result is that the acids produce an excessively high conductivity reading, which can be mistaken for a very large TOC concentration. If this error is to be avoided, a complex algorithm must be used to detect conductivity peaks. This algorithm extends the length of the oxidation period to estimate steady-state conductivity that will be achieved when acids are completely oxidized to carbon dioxide. This algorithm increases the complexity of the analyzer, increases cost of the electronics, and makes the duration required for each measurement unpredictable.

Locating and operating conductivity electrodes in the UV reactor also produces hydrogen peroxide that can oxidize organics, even before the UV lamp is turned on. Acids produced in this oxidation increase conductivity of the water while initial conductivity measurements are made to determine IC concentration. This causes a positive error in IC measurement and a negative error in TOC measurement.

Having electrodes and other materials, other than quartz, in the UV reactor also produces errors due to leaching of ions into water. These ions increase conductivity of water, causing errors in measurement of both IC and TC.

In the method of Egozy, resistivity, following oxidation for an infinitely long period, is estimated from several measurements made for several different oxidation periods. Projected resistivity for infinitely long oxidation periods is then used to calculate TOC of the solution. One disadvantage of this method is that the TOC calculation is performed only after several measurements are made, making the method very slow. Another disadvantage is that projection of resistivity for infinitely long oxidation periods cannot be made if composition of water samples change while measurements are being made. Therefore, this method cannot be used on process streams that even change their composition very slowly.

SUMMARY OF THE INVENTION

Advantages of the Invention

The present invention has none of the problems of known continuous-flow and stop-flow TOC analyzers, and all of their advantages. Unlike the continuous-flow approach, a small, inexpensive UV reactor can be used to completely oxidize organics to carbon dioxide because the time that the water sample is exposed to UV light is controlled by operation of a solenoid valve. No expensive flow- or pressure-control components are required, and no operator intervention is needed to maintain a fixed flow rate.

The present invention also has better accuracy than the stop-flow approach because conductivity electrodes are located outside the UV reactor, where UV light cannot illuminate them. This avoids any possibility of unwanted photochemical reactions. The UV reactor is constructed entirely of quartz to eliminate leaching of extraneous ions into the portion of the sample in which organics are to be oxidized. Furthermore, in a preferred embodiment, pulsed flow of sample water occurs before conductivity measurements begin. This ensures that any ions leached from conductivity electrodes are swept away from the electrodes prior to the measurements.

Such preferred embodiment additionally has the advantage that its design can be implemented using unusually inexpensive manufacturing techniques that reduce material costs and assembly labor, and increase reliability of the instrument. Such preferred embodiment has an advantage related to maintainability, because the conductivity cell is removable from the UV reactor. Either part can be easily removed for maintenance or replacement when necessary.

In its broadest embodiment, the apparatus of the present invention comprises:
  an organic carbon irradiation chamber having a fluid inlet conduit and a fluid exit conduit, wherein at least part of said chamber is substantially permeable to radiation capable of generating radiation-initiated products of said organic carbon,
  said fluid exit conduit being in fluid communication with measuring means effective to measure one or more of said products,
  means to provide a stream of said water, and
  means effective to provide seriatim the following steps:
    (a) flowing said stream seriatim through said inlet conduit, said chamber, said exit conduit and said measuring means, thereby at least partly filling said chamber with said water;
    (b) stopping flow of said stream, whereby said chamber remains at least partly filled with said water;
    (c) irradiating said water in said chamber with said radiation for a first predeterminable time and temperature effective to produce products of said organic carbon in said water, thereby producing irradiated water;
    (d) flowing at least part of said irradiated water into said measuring means;
    (e) stopping flow of said irradiated water into said measuring means, whereby said measuring means retains part of said irradiated water
    (f) effecting a measure of one or more of said products in said measuring means, thereby producing a first measure of said products;
  said apparatus further comprising one or more additional means selected from the group consisting of:
    A. estimating means for estimating said organic carbon content at least in part from said first measure, thereby producing an estimate of said organic carbon content
    B. displaying and/or recording means for displaying an estimate of said organic carbon content.
    C. first measure comparing means for comparing said first measure with a predeterminable value of said first measure.

D. logic means for estimating said organic carbon content at least in part from said first measure, thereby producing an estimate of said organic carbon content, and for comparing said estimate with a predeterminable value of said estimate E. irradiating means for irradiating said water in said chamber with radiation effective to react said organic carbon substantially to carbon dioxide, carbonic acid and/or bicarbonate, and to predetermine said first predeterminable time and temperature at values sufficient to react said organic carbon substantially to carbon dioxide, carbonic acid and/or bicarbonate as products of said organic carbon in said water.

F. shielding means effective substantially to shield said measuring means from said radiation G. temperature and electrical conductivity and/or electrical resistance detecting means in said measuring means H. temperature and electrical conductivity and/or electrical resistivity detecting means in said measuring means, said detecting means comprising stainless steel electrodes immersible in fluid in said measuring means, I. irradiating means for irradiating said water in said chamber with radiation including wavelengths less than and equal to 254 nanometers, J. irradiating means for irradiating said water in said chamber with radiation including wavelengths in the range of from about 160 nanometers to about 200 nanometers, and, K. stepping means to provide seriatim steps including a step flowing said stream seriatim through said inlet conduit, said chamber, said exit conduit and said measuring means, thereby at least partly filling said chamber with said water; a step stopping flow of said stream whereby said chamber remains at least partly filled with said water; a step retaining water from said last mentioned step in said chamber for a second predeterminable time and temperature in the absence of irradiating said water with said radiation; a step flowing at least part of water retained in said chamber in said last mentioned step into said measuring means and stopping flow of said water, whereby said measuring means retains part of said water; a step effecting a measure of said one or more of said products in water retained in said measuring means in said last mentioned step.

In its broadest embodiment, the process of the present invention comprises:

estimating organic carbon content of a stream of water using an organic carbon irradiation chamber having a fluid inlet conduit and a fluid exit conduit, wherein at least part of said chamber between said inlet and outlet conduits is substantially permeable to radiation capable of generating radiation-initiated products of said organic carbon, said fluid exit conduit being in fluid communication with a measurement system to measure one or more of said radiation-initiated products or said organic carbon, the process comprising seriatim the following steps:

(a) flowing said stream seriatim through said fluid inlet conduit, said irradiation chamber, said fluid exit conduit, and said measurement system, thereby flushing said conduits, said chamber and said measurement system, and at least partly filling said chamber with said water;

(b) stopping flow of said stream, whereby said chamber remains at least partly filled with said water;

(c) irradiating said water in said chamber with said radiation at least through said part of said chamber substantially permeable to said radiation for a first predeterminable time and temperature to generate radiation-initiated products of organic carbon in said water in said chamber, thereby producing irradiated water, (d) flowing at least part of said irradiated water into said measurement system;

(e) stopping flow of said irradiated water into said measurement system, whereby part of said irradiated water is retained in said measurement system;

(f) measuring said one or more of said radiation-initiated products of said organic carbon in said part of said irradiated water, thereby producing a first measure of said radiation-initiated products;

(g) estimating said organic carbon content at least in part from said first measure, thereby producing an estimate of said organic carbon content; and, (h) transmitting by means of electrical signal and/or displaying and/or recording said estimate.

The process of this invention may further comprise the additional steps of:

(i) retaining said water from step (b) in said chamber without irradiating said water with said radiation for a second predeterminable time and temperature, thereby producing non-irradiated water;

(j) flowing at least part of said non-irradiated water from step (i) into said measurement system;

(k) stopping flow of said non-irradiated water into said measurement system, whereby part of said irradiated water is retained in said measurement system;

(l) measuring said one or more of said radiation-innitiated products of said organic carbon in said part of said non-irradiated water, thereby producing a second measure of said radiation-initiated products;

(m) estimating said organic carbon content at least in part from said first measure and said second measure, thereby producing an alternative estimate of said organic carbon content; and, (n) transmitting by means of electrical signal and/or displaying and/or recording said alternative estimate.

BRIEF DESCRIPTION OF THE DRAWINGS

FIG. 1 illustrates a preferred process flow configuration for the present invention showing essential mechanical components and electronics.

FIG. 2 illustrates a preferred system for measurement of conductivity and temperature.

FIG. 3 also illustrates a preferred embodiment of the present invention wherein components of FIG. 2 are included.

FIG. 4 illustrates an analysis sequence in accordance with the present invention.

FIG. 5 is a graph illustrating actual measurements of ultrapure water samples using the apparatus and methods of the invention.

DETAILED DESCRIPTION OF PREFERRED EMBODIMENTS

A preferred configuration of the invention consists of the mechanical components shown in FIG. 1, plus electronics necessary to (1) make conductivity and temperature measurements, (2) operate the UV lamp and on/off (e.g., solenoid) valve, and (3) calculate TOC concentrations. Hardware shown in FIG. 1 consists of an inlet 1 connected to the water source (not shown), optionally a filter 2, UV reactor 3, one cell for measurement of electrical conductivity and/or electrical resistivity 4 (preferably having a temperature sensor 5), on/off (e.g., solenoid) valve 6, and outlet 7 through which analyzed water is discharged.

FIG. 2 shows a UV lamp 8, UV reactor 3, and cell 4 for measurement of conductivity and temperature. Water enters the cell and preferably passes through a filter 2, which may be replaceable. Such water continues into UV reactor 3, which may be fabricated from two pieces of flat quartz or glass. At least part of the surfaces of such reactor is substantially transparent to radiation for effecting oxidation of organic carbon, preferably effecting oxidation to free carbon dioxide, carbonic acid and/or bicarbonate, which together are generally referred to herein collectively as "carbon dioxide." In a preferred embodiment, the water cavity is formed in a thicker piece of such quartz or glass. The water cavity is covered with a thinner piece of UV-transmitting quartz or glass. The two pieces are bonded together such that water cannot escape from the water cavity except through an entrance and exit hole in the UV reactor.

UV light source 8 irradiates water in the UV reactor 3, through an opening in housing 9. This opening restricts the UV light to irradiating only the water in a portion of the UV reactor 3. The UV source 8 illuminates the UV reactor 3 with light having wavelengths effective to oxidize organics, preferably to form carbon dioxide. Preferably, said radiation includes wavelengths less than and equal to 254 nanometers (the principal emission line of the low pressure mercury vapor lamp), more preferably wavelengths in the range of from about 160 nanometers to about 200 nanometers. The latter may be obtained, for example, from medium or low pressure mercury vapor lamps or certain excimer lamps, constructed from materials such as synthetic silica and fused quartz. The free carbon dioxide preferably formed reacts with water, ultimately to form hydronium and bicarbonate ions, which increase conductivity of the solution. The UV light source 8 is mounted in a second housing 10, separated from the first housing 9 by a gasket 11.

After irradiation in the UV reactor 3, water passes into conductivity and temperature measurement cell 4. This cell contains two electrodes 12 mounted in a nonconductor, such as plastic. The electrodes 12 are preferably stainless steel, and are shielded from UV light by the opening in housing 9 and by multiple bends in the water passage. A temperature sensor 5 is located outside the cell 4, but close to one of the conductivity electrodes. Proximity to the metal electrode provides effective heat transport from water to the temperature sensor 5 for accurate temperature measurements. After conductivity and temperature measurement, such water exits the cell 4.

The electrodes 12 in conductivity and temperature measuring system 4 are preferably stainless steel electrodes because stainless steel is inexpensive and corrosion resistant under conditions existing in such measuring means. Other nickel-bearing corrosion resistant metals, including nickel itself, can also be used as well as other corrosion resistant metals. Noble metals including noble-metal-coated base metals are not preferred because of their higher cost.

Electrodes 12 are shielded from UV radiation in preferred embodiments. Nevertheless, water which has been irradiated in UV reactor 3 may contain residual trace amounts of hydrogen peroxide or other oxidants. The electrode materials are preferably substantially inert to such oxidants, including not absorbing the latter, and not forming active oxidizing species on the electrode surfaces. Such absorbed oxidants and/or active oxidizing species, if not destroyed by the conductivity measurement, may give rise to trace oxidation of organics in a subsequent measurement of conductivity of non-oxidized water.

Temperature and conductance and/or resistance measuring system 4 broadly include the measuring circuits and electronics. The latter may for example apply a constant audio frequency current (e.g., 1 KHz) and measure the voltage required to obtain such current, or apply a constant audio frequency voltage measuring the current thereby obtained, in either case preferably correcting for capacitance or reactance in the measuring circuit.

Although the temperature and conductance and/or resistance measuring system 4 has been described in terms of electrodes 12, such system 4 may also comprise an electrodeless system, particularly advantageous in this invention. Such electrodeless system includes measuring reactive losses in system 4 or coupling between coils wound around system 4, both well known in the art.

Many organics are not well oxidized by the 254 nanometer principal line of the low pressure mercury vapor lamp in the absence of photocatalysts in reactor 3. It is preferred therefore to use as UV light source 8 a source producing radiation effecting oxidation of substantially all organic carbon, more preferably effecting oxidation of substantially all organic carbon to free carbon dioxide, carbonic acid and/or bicarbonate (collectively "carbon dioxide" herein). Such sources produce substantial amounts of radiation having wavelengths less than such 254 nanometers, more preferably substantial amounts in the range of from about 160 to about 200 nanometers. Suitable sources for radiation in this range of wavelengths include medium and low pressure mercury vapor lamps constructed from materials such as synthetic silica and fused quartz, and certain coherent or incoherent excimer lamps (e.g., lamps based on xenon) constructed from the same materials.

In a preferred embodiment, an electrical contact 13 is provided to ground housing 10 in event of a short circuit in wiring connected to UV light 8.

FIG. 3 shows a preferred embodiment of the invention with certain identified components shown in FIG. 2 mounted in conjunction with the solenoid valve 6 on a board 14 containing electronics required to operate the solenoid valve 6, UV lamp 8, and conductivity and temperature measurement cell 4. Water enters inlet 1 when valve 6 is open, and enters UV reactor 3 and conductivity and temperature measurement cell 4. UV lamp 8 is in housing 10, which is mounted on housing 9 by means of spring 15. After the conductivity and preferably temperature of the water have been measured, water flows through tube 16 into solenoid valve 6. When the water passes through solenoid valve 6, it is discharged from the apparatus through outlet 7. Electronics on board 14 receive electrical power and transmit data through electrical connector 17. Electrical power is provided to UV lamp 8 through electrical connector 18.

To make a TOC measurement, a sequence such as that shown in FIG. 4 may be used. Such analysis sequence starts with a "flush" during which the UV lamp is off and the solenoid is activated (open). Water from the water source flows through the UV reactor and measurement cell. Such flush also rinses out inlet tubing. At the end of the flush, the solenoid valve is closed, providing a new sample in the UV reactor, ready for analysis.

The solenoid valve then remains closed for a period such as 180 sec. The UV lamp is on only during this organic oxidation period. Upon completion of such oxidation period, the UV lamp is turned off, and the solenoid valve is opened for a brief period (0.010 to 1 sec., depending on the sample flow rate). Under the influence of the pressure drop across the apparatus, the solenoid valve allows water from the UV reactor to move into the conductivity and temperature measurement cell. This brief opening of the solenoid valve is followed by a measurement period, such as 10 sec. During the measurement period, conductivity and temperature of the water are measured.

Following such measurement period, the solenoid valve opens, providing another flush. Following such second flush, the solenoid valve closes, and the fresh portion of water sample is then retained in the UV reactor with the UV lamp off for about the same length of time as the oxidation period (and at about the same temperature). The solenoid valve opens again for 0.010 to 1 sec. when such period is completed. This short opening of the solenoid valve allows non-oxidized water in the inactive UV reactor to move into the measurement cell, where temperature and conductivity are measured again as above. The two temperature-corrected conductivity measurements are then used to calculate with extremely high accuracy the TOC concentration in the water sample. The present invention transmits the calculated TOC concentration by electrical signal.

Further embodiments and/or aspects of the apparatus and/or process of this invention include:
(a) Omitting the temperature measurement, in which case conductance and/or resistance measurements, uncompensated for temperature, are used to calculate the TOC concentration.
(b) Omitting the cycle in which non-irradiated water sample is produced and its conductance and/or resistance is measured. Such embodiment is useful when it is known that the correction for the non-irradiated sample is negligibly small compared to the accuracy desired for determining organic carbon content. Such omission permits more frequent estimates of organic carbon content and further simplifies the electronics.
(c) If such cycle (in which a non-irradiated sample is produced) is not omitted, then the apparatus can display and/or record (locally in or near such apparatus or remotely) and/or transmit electrically either the organic carbon content corrected for such non-irradiated sample or both the corrected and uncorrected values. In some applications, this additional information displayed is useful.
(d) For some uses of the apparatus and process of the present invention, it is desirable to generate a signal if the organic carbon content estimated by the apparatus and process is more than, or is less than, a predeterminable value of such estimate. For example, it may be sufficient if the apparatus and process energize a green light emitting diode if the organic carbon content estimated is less than a predeterminable value and/or energize a red light (and/or an audible alarm) if the content estimated is greater than such predeterminable value. For such uses it may not be necessary to display a (corrected and/or uncorrected) estimate of organic carbon content, in which case the above signals may be generated directly from (corrected or uncorrected) conductances and/or resistances without calculating corresponding organic carbon contents.
(e) The apparatus and process of the invention have been described and/or exemplified using electrical conductance and/or electrical resistance as a technique for determining the products of irradiation of organic carbon. For some uses of the apparatus and process of the present invention, it may be useful if such irradiation does not convert such organic carbon substantially to free carbon dioxide, carbonic acid and/or bicarbonate. It has also been observed above that such electrical conductance and/or electrical resistance may be determined with electrodeless methods. For some uses of the apparatus and process it may be useful to use techniques other than, or in addition to, measurement of conductance and/or resistance for determining the products of irradiation. For example, pH; oxidation-reduction potential ("ORP"); electrochemical techniques, including voltammetry, amperometry, potentiometry, membrane-covered electrodes, and coulometry; colorimetry; spectrophotometry; titrations; and other well-known techniques may be used to make such measurements. In such cases it will generally be advantageous for the flow of irradiated and/or non-irradiated sample to be stopped in the measurement means during the measurement.

Test Results

Actual measurements of ultrapure water samples and samples containing sucrose at various TOC concentrations have been made (see FIG. 5). Results obtained with the invention are compared to measurements made with a commercial TOC analyzer (Sievers® Model 800 TOC Analyzer). These results are substantially linear and accurate to well within ±15%.

The preferred embodiment was tested with a variety of organic compounds, which were selected because they either are commonly used to calibrate TOC analyzers (for example, sucrose) or because they represent types of compounds that would likely be found in water produced by an ultrapure water system if the system failed or required maintenance. For example, sodium poly 4-styrene sulfonate and similar compounds leach from cation exchange resins used in water systems, especially when the resin nears the end of its life. N,N-dimethylethanolamine is an example of a class of compounds that leaches from anion exchange resin as the resin degrades. Acetone, isopropanol, and methanol commonly are contaminants in feed water, but they also may leach into water from plastics and similar sources within the water system. Humic acid and urea are naturally occurring compounds found in feed water.

The present invention responds to organic compounds that contain hetero-atoms (e.g., N, S, P, and halides) differently than it does to organics that do not contain hetero-atoms. Therefore, its response to the following compounds would be expected to demonstrate positive or negative errors, depending on the compound and its concentration:
1. Sodium poly 4-styrene sulfonate
2. N,N-Dimethylethanolamine
3. Humic acid
   (Humic acids contain 2 to 4% N and 1 to 2% S by weight, per Snoeying, V. L. and Jenkins, D., Water Chemistry; John Wiley & Sons, New York; p. 233; 1980.)
4. Urea A preferred embodiment of the invention was used after it had been calibrated. Table 1 shows results of the testing. It is clear that the present invention is able to detect all of the tested compounds. Therefore, this test proves that the invention is a valuable tool for detecting water impurities when a water system is in need of repair or maintenance. Furthermore, a failure of a water system would result in a combination of organics passing through into product water, not just a single compound. Therefore, results of this test also show that the invention will produce a significant response to that mixture of organics, even if its response to some of them errs on the negative side.

TABLE 1
RESPONSE TO SELECTED ORGANICS

| COMPOUND | MEASURED TOC, ppb | ACTUAL TOC CONCENTRATION, ppb[a] | DIFFERENCE, % |
|---|---|---|---|
| Acetone | 193 | 208.0 | -7.2 |
| N,N-Dimethyl-ethanolamine | 60 | 67.2 | -10.7 |
|  | 118 | 164.3 | -28.2 |
| Humic acid | 21 | 37.0 | -43.2 |
| Isopropanol | 56 | 60.5 | -7.4 |
|  | 195 | 198.0 | -1.5 |
| Methanol | 60 | 64.3 | -6.7 |
|  | 171 | 195.5 | -12.5 |
| Sodium poly 4-styrene sulfonate | 87 | 84.5 | 3.0 |
|  | 337 | 236.7 | 42.4 |
| Sucrose | 47 | 54.3 | -13.4 |
|  | 178 | 203.0 | -12.3 |
| Urea | 128 | 47.5 | 169 |
|  | 1,223 | 148.7 | 722 |

[a] As measured using a Sievers ® Model 800 TOC Analyzer.

Summary of Advantages of Invention Over Former Methods

In the present invention, conductivity electrodes are not located in the UV reactor, or otherwise located where UV light will strike them. This avoids undesirable photochemical reactions leading to IC and TC measurement errors.

In the present invention, the conductivity and temperature measurement cell can be removed from the UV reactor for cleaning or replacement when required.

In the present invention, the UV reactor is preferably constructed entirely of quartz and/or glass (both transparent at least in part to radiation capable of effecting oxidation) so that no significant concentration of ions leaches into solution to be oxidized. This also avoids IC, TC, and TOC measurement errors.

In the present invention, exposure to UV is sufficient for oxidation of organics at least partially to carbon dioxide, even in a small, inexpensive reactor.

The present invention is also able to control the length of UV exposure and the length of temperature and conductivity measurements with very simple and inexpensive hardware. This results in a smaller, more reliable, more maintainable analyzer than former methods. It also allows use of slower, more inexpensive measurement electronics.

The present invention is able to accommodate relatively large changes in available water pressure drop without need to change duration of the various periods during which the solenoid valve is open. This is because the wetted volume of the UV reactor preferably has been selected to be much larger than the wetted volume of the conductivity cell. Thus, no operator labor is required for normal variations in available water pressure drop. The latter may be provided by any means upstream, within, or downstream of the apparatus.

In applications in which the available water pressure drop varies even more, the invention can be operated in such a way that information on such pressure drop can be obtained to adjust the timing of operation of the solenoid valve. Such information can be either obtained, for example, from the operator, or the apparatus can measure the time the solenoid valve must be open so that ionized, oxidized compounds from the UV reactor are captured in the conductivity measurement cell. Yet another example is that the apparatus of the present invention can measure the time the solenoid valve must be open so that, when oxidized water is captured in the conductivity and temperature measurement cell, the measured temperature is maximized. The second and third examples would allow periodic, automatic adjustment of the solenoid valve operation to be made to accommodate larger changes in available water pressure drop.

The apparatus of the present invention consumes less water during analysis, which is especially useful for small water purification systems. Therefore, the productivity of water purification systems that employ the invention is greater than with prior art methods.

Differentiation of Invention Over Prior Art Methods and Apparatus

Takahashi U.S. Pat. No. 4,749,657

In Takahashi '657, a sample flows continuously through a UV reaction zone, in the presence of oxygen, and is partially but not completely oxidized to carbon dioxide, and conductivity of the partially oxidized organics is measured in a conductivity cell. An inlet conductivity cell also may be employed to determine original conductivity of the solution. Gases also may be sparged from the sample prior to initial conductivity measurement.

Some key differences between the present invention and the Takahashi device are:

a. The present invention does not use continuous flow thereby avoiding the problem of controlling flow rate accurately.

b. The present invention effects substantially complete oxidation of organics to carbon dioxide, although it could be configured for very fast response if shorter oxidation periods were used, which would result in incomplete oxidation, and this allows the invention be used as a fast-response detector of organic concentration spikes (upsets) in some process streams.

c. The addition of oxygen to the water sample in the present invention is generally not required.

Chubachi U.S. Pat. No. 5,518,608

Chubachi '608 describes a plant for producing and using ultrapure water, consisting of a first TOC monitor, a water purifier containing ion exchange resins, and a second TOC monitor. The TOC concentration in the purifier output water is continuously monitored to allow early detection of when performance of the ion exchange resin has deteriorated. The "TOC monitors" referred to are identified as resistivity sensors elsewhere in the patent.

The Chubachi analyzer seems generally similar to the Takahashi apparatus. The differences between Chubachi '608 and the present invention are correspondingly the same as those cited above for the Takahashi '657 patent.

Blades U.S. Pat. No. 4,868,127

Blades '127 discloses a UV oxidation cell containing a window, a pair of conductivity electrodes therein, and a source of UV light shining through such window.

Also disclosed are:

(i) a conductivity cell at the inlet of a separate UV reaction chamber, which contains catalyst for organic oxidation, with a second conductivity cell located on theoutlet of the UV reaction chamber, the responses of the two conductivity cells being compared to determine organic carbon concentration;

(ii) conductivity electrodes having photocatalytic coatings in the UV reactor, positioned so they are exposed to UV light, catalyzing the organic oxidation;

(iii) a method for measuring TOC in deionized water, in which water is in contact with conductivity electrodes having a catalytic coating and exposed to UV light. The electrode surfaces catalyze the organic oxidation;

(iv) a cell containing conductivity electrodes exposed to UV light and having an electrical potential applied to the electrodes to cause electrophoresis to take place; and, (v) a cell containing electrodes exposed to UV light specified as 170–190 nm.

The main differences between the present invention and the Blades '127 patent are:

a. The UV reactor of the present invention does not require catalyst for organic oxidation.

b. Conductivity electrodes of the present invention are not located where organic oxidation occurs.

c. Conductivity electrodes of the present invention are located where they are not exposed to UV light.

d. Conductivity electrodes of the present invention are preferably constructed from stainless steel, which is well known not to catalyze oxidation of organics when exposed to UV light.

e. Measurement of conductivity with the present invention is made only when UV light is turned off.

f. No electrical potential is applied to the electrodes of the present invention for the purpose of causing electrophoresis.

g. Only one conductivity cell is needed in the present invention.

Blades U.S. Pat. No. 5,275,957

Blades '957 describes a sample cell for measuring TOC containing a pair of conductivity electrodes. Conductivity and temperature are measured repetitively to yield a series of values for carbon dioxide content of the water analyzed. Also disclosed are:

(i) a method in which the conductivity and temperature are repetitively measured in order to calculate the original TOC concentration in the water;

(ii) the addition of a temperature sensor in vicinity of the sample water;

(iii) an apparatus consisting of a sample cell containing catalyst for oxidation of organics, and in which temperature and conductivity are measured; and, (iv) an apparatus consisting of a sample cell irradiated with UV light, and means to repetitively measure conductivity and temperature to calculate by extrapolation the amount of carbon dioxide in the water during the oxidation process.

The key differences between the present invention and the Blades '957 patent are:

a. Conductivity electrodes of the present invention are not located where organic oxidation occurs.

b. Conductivity electrodes of the present invention are located where they are not exposed to UV light.

c. Measurement of conductivity in the present invention is made only when UV light is turned off.

d. Conductivity and temperature in the present invention are not measured repetitively in a single water sample as oxidation proceeds.

h. The UV reactor of the present invention does not contain catalyst for organic oxidation.

e. Conductivity electrodes of the present invention are preferably constructed from stainless steel, which is known not to catalyze oxidation of organics when exposed to UV light.

Melanson U.S. Pat. No. 5,677,190

The Melanson '190 patent pertains to the design and assembly of a TOC cell, including:

(i) An elongated generally tubular member defining an elongated internal sample volume, the member comprising a tube of a fusible material transparent to UV radiation selected from the group consisting of glass, fused silica or fused quartz;

(ii) First and second end members formed of a material fusible to the material of such tubular member, such end members fused to such tubular member, delimiting ends of the sample volume; and, (iii) A pair of elongated continuous rod electrodes supported by such end members spaced from and parallel to one another along an axis of elongation of the tubular members, within the sample volume, first ends of the electrodes supported by the first end member, being sealed thereby within the internal volume, and second ends of the electrodes extending through and sealed to the second end member, such that electrical conductors may be connected directly to such second ends of the electrodes for connection to external circuitry for monitoring electrical characteristics of a fluid in such internal volume during exposure to radiation.

Also disclosed is a method of making a cell for containing a sample of liquid while simultaneously irradiating liquid in the cell with radiation of predetermined wavelength from a source, and monitoring a predetermined electrical characteristic of the liquid.

Differences between the present invention and the design described in the Melanson '190 patent are:

a. The electrodes of the present invention are not arranged along an axis of elongation of "tubular members" within the sample volume that is exposed to UV radiation.

b. The electrodes of the present invention are not irradiated by UV radiation.

c. The electrodes of the present invention are located in a housing, which can be removed from the UV reactor.

d. The sample volume in the present invention is preferably delimited by a cavity in a rectangular piece of material. The material itself may be substantially transparent to radiation effective to cause oxidation of organics, at least on the side of the cavity irradiated by such radiation, or the cavity may be covered by material substantially transparent to such radiation, if such covering material is irradiated by such radiation. Suitable materials are those substantially transparent to wavelengths less than 254 nanometers (the wavelength of the principal line of the low pressure mercury vapor lamp). Preferable materials are transparent to wavelengths in the region of from about 170 to about 200 nanometers. Suitable materials include without limitation quartz and vitreous silica which have not been doped to absorb wavelengths less than 254 nanometers.

e. Conductivity and temperature measurements in the present invention are not measured repetitively in a single water sample as oxidation proceeds.

f. In the present invention, the electrodes are preferably stainless steel, molded into a suitable housing removable from the UV reactor. The electrodes extend out of the housing, where electrical contact is made to them.

Egozy U.S. Pat. No. 5,272,091

The Egozy '091 patent discloses a method for predicting organic carbon content consisting of exposing water to oxidation for a series of different time periods. This allows measurements to be extrapolated to a situation in which the oxidation period is infinitely long.

Apparatus is disclosed for doing this, having a three-way valve downstream from an inlet conductivity cell, and between that conductivity cell and an oxidation zone. A second conductivity cell is located at the outlet of such oxidation zone. This allows sample conductivity to be monitored before oxidation in the first conductivity cell, and the residence time in the oxidation zone to be controlled by the timing of the three-way valve. Conductivity of the sample after oxidation is measured by the second conductivity cell.

Key differences between the current invention and such Egozy '091 patent include:
 a. The present invention uses a single conductivity cell.
 b. The present invention locates the valve downstream of the UV reactor and conductivity cells. The Egozy '091 patent locates the three-way valve upstream of the oxidation zone and the second conductivity cell.
 c. The present invention uses a relatively simple on/off valve, rather than a more complex three-way valve.
 d. The present invention does not involve a use of a series of different oxidation periods to do any calculations. The oxidation period is pre-set, and not changed by the operator.

Voss Publication WO 99/42824

In Publication WO 99/42824 (and the related DE 198 06 854 A1), Voss discloses:
 (i) a method in which a volume of liquid is retained in a reaction chamber, where said liquid is oxidized. Following oxidation, said liquid flows through a measurement cell, while repetitive measurements (preferably conductivity but not temperature) are made. The repetitive measurements are used to calculate a response peak, and organic carbon concentration is estimated from the peak height. The baseline under the peak is measured to determine the inorganic carbon concentration in the liquid. Voss discloses that the oxidation of organics may be achieved by a UV lamp immersed in the liquid;
 (ii) a method in which a volume of liquid is retained in the reaction chamber, where said liquid is oxidized. Following oxidation, said liquid flows through a measurement cell, while repetitive measurements are made. The repetitive measurements are used to calculate a response peak, and organic carbon concentration is estimated from the peak area. The baseline under the peak is measured to determine the inorganic carbon concentration in the liquid; and,
 (iii) an apparatus for measuring the organic carbon content of liquids, implementing the methods described above.

The differences between the present invention and the Voss publication are:
 a. In the present invention, measurements are not made repetitively in a single water sample. The Voss methods and apparatus require more costly electronics because of the need to make repetitive measurements, store the results of those measurements, and calculate the height and/or area of the response peak using complex differentiation and/or integration algorithms.
 b. The present invention uses a second measurement of conductivity and temperature, on a non-irradiated water sample, to measure the background inorganic carbon concentration in the water. The Voss methods and apparatus must measure the inorganic carbon concentration by determining the baseline of the response peak, using complex algorithms and costly electronics.
 c. In the present invention, measurements are made while the water sample is stopped in the conductivity cell, not while it is flowing. Therefore, the present invention is more accurate than the Voss methods and apparatus, which are subject to significant errors when the flow rate of liquid changes during the measurement, especially when peak area is measured.
 d. The present invention measures temperature along with conductivity, so that carbon measurements are accurately compensated for changes in the temperature of the water and ambient environment. The Voss methods and apparatus are much less accurate and less dependable because of the inability to compensate for temperature changes.
 e. The UV lamp in the present invention is not immersed in the water sample. This permits the use of a smaller, less expensive apparatus than does the Voss publication, which discloses the UV lamp immersed in the water sample.
 f. Because the UV lamp in the present invention is not immersed in the water sample, cold water will not reduce the amount of UV light irradiating the sample. By contrast, the Voss apparatus has the UV lamp immersed in the water sample, and. as a result less UV radiation reaches the water sample when the water is cold. It is well known that cooling reduces the radiation produced by UV lamps.

Each of the foregoing prior art patents, publications and literature references cited above and in the Background of the Invention is incorporated herein by reference.

Alternate Embodiments of the Present Invention

By modifying the electrical circuitry, it is possible to make the conductivity measurements according to the present invention without the electrodes being in contact with the water. With such modification, the electrodes could be placed on the outside of the water stream. This could potentially increase reliability, reduce assembly labor, and possibly reduce total cost.

In another embodiment, the conductivity cell could be separated from the UV reactor by tubing and fittings. This is not generally a preferred embodiment because of cost and reliability issues.

The present invention could be operated at many different temperatures. Although testing reported herein has been done at room temperature, the oxidation kinetics would be expected to be better at somewhat elevated temperatures. This offers the possibility of still faster TOC measurements.

The configuration of the UV reactor and conductivity cells according to the present invention could be altered in many ways. For example, the UV reactor could be tubular instead of the flat, rectangular geometry illustrated and described herein.

The invention could be operated to obtain measurements in much less than 3 min. It is expected that in this embodiment, the result of the organic oxidation only partly would be carbon dioxide. Organic acids also would be produced by some organic solutes. These acids also can be measured using conductivity in accordance with this invention.

Novel Features of the Present Invention

Some of the principal novel features of the present invention are summarized below:
 a. The use of the pulsed-flow technique, described above, to control the residence time of the sample water in the UV reactor without the use of expensive and complex flow- and pressure-control components. At the same time, the pulsed-flow technique of this invention eliminates errors in TOC measurement that arise from photochemical production of ions when the conventional stop-flow technique is used.

b. The pulsed-flow technique also has the novel feature that temperature and conductivity measurement times can be set to relatively long periods. This allows slower electronic components to be used in the measurement circuitry, which minimizes the cost of that circuitry.

c. The design of the measurement cell is compatible with insert molding techniques that can result in a very inexpensive and highly reproducible cell. Assembly labor is minimal because electrodes can be sealed into the cell during the molding process.

d. The design of the UV reactor. This laminated design is simple, small and inexpensive. The ability to make fluidic connections is especially reliable and inexpensive.

e. The possibility of automated adjustment of solenoid pulses to accommodate changes in the pressure of the water sample.

Commercial Applications

The present invention is ideally suited for use in applications where monitoring water for organic contaminants is required, the water is of at least deionized quality, and where the cost of more sensitive or accurate instrumentation is not justified. A specific application is in laboratory ultrapure water systems. Furthermore, the low cost and simplicity of the present invention make it possible to provide it to original equipment manufacturers of those laboratory water systems.

It will be apparent to those skilled in the art that other changes and modifications may be made in the above-described apparatus and methods for pulsed-flow total organic carbon analysis without departing from the scope of the invention herein, and it is intended that all matter contained in the above description shall be interpreted in an illustrative and not a limiting sense.

What is claimed is:

1. Apparatus for estimating the organic carbon content of water, said apparatus comprising:

an organic carbon oxidation chamber having a fluid inlet conduit, a fluid exit conduit, and a surface therebetween, wherein at least part of said surface between said inlet and outlet conduits is at least substantially transparent to radiation capable of effecting oxidation of said organic carbon;

said fluid exit conduit is in fluid communication with an electrode system effective to measure electrical conductance and/or electrical resistance of a fluid;

a fluid source to provide a stream of said water to said organic carbon oxidation chamber;

said apparatus further comprising a fluid flow control and measurement system comprising a combination of elements to effect the following steps seriatim:

(a) flowing said stream seriatim through said fluid inlet conduit, said oxidation chamber, said fluid exit conduit and said electrode system, thereby flushing said conduits, said chamber and said electrode system and at least partly filling said chamber with said water;

(b) stopping flow of said stream whereby said chamber remains at least partly filled with said water;

(c) irradiating said water in said chamber with said radiation at least through said part of said surface for a first predeterminable time and temperature to effect oxidation of organic carbon in said water in said chamber thereby producing irradiated water;

(d) flowing at least part of said irradiated water into said electrode system;

(e) measuring electrical conductance and/or electrical resistance of said part of said irradiated water in said electrode system, thereby producing a first electrical conductance and/or a first electrical resistance; and, (f) estimating said organic carbon content at least in part from said first electrical conductance and/or said first electrical resistance.

2. Apparatus according to claim 1 in which said apparatus further comprises additional fluid flow control and measurement elements to effect the following steps seriatim:

(g) retaining said water from step (b) in said chamber without irradiating said water with said radiation for a second predeterminable time and temperature, thereby producing non-irradiated water;

(h) flowing at least part of said non-irradiated water from step (g) into said electrode system;

(i) measuring electrical conductance and/or electrical resistance of said part of said non-irradiated water in said electrode system thereby producing a second electrical conductance and/or a second electrical resistance; and, (j) estimating said organic carbon content at least in part from said first electrical conductance and/or first electrical resistance, and at least in part from said second electrical conductance and/or second electrical resistance.

3. Apparatus according to claim 1 further comprising a radiation source in alignment with said surface to provide radiation effective to oxidize said organic carbon substantially to free carbon dioxide, carbonic acid and/or bicarbonate.

4. Apparatus according to claim 1 further comprising a radiation source in alignment with said surface to provide radiation effective to oxidize said organic carbon substantially to free carbon dioxide, carbonic acid and/or bicarbonate, and in which said first predeterminable time and temperature are sufficient to effect oxidation of organic carbon in said water substantially to free carbon dioxide, carbonic acid and/or bicarbonate.

5. Apparatus according to claim 2 wherein said flow control and measurement system is set to establish said second predeterminable time and temperature substantially equivalent to said first predeterminable time and temperature.

6. Apparatus according to claim 3 wherein said flow control and measurement system is set to establish said second predeterminable time and temperature substantially equal to said first predeterminable time and temperature.

7. Apparatus according to claim 1 wherein said apparatus further comprises a shield effective substantially to shield said electrode system from said radiation.

8. Apparatus according to either of claim 1 or claim 2 wherein said electrode system is juxtaposed relative to said fluid exit conduit.

9. Apparatus according to either of claim 1 or claim 2 wherein said electrode system is juxtaposed relative to said fluid exit conduit and detachable therefrom.

10. Apparatus according to either of claim 1 or claim 2 wherein said electrode system comprises at least two electrodes immersible in said fluid.

11. Apparatus according to either of claim 1 or claim 2 wherein said electrode system comprises at least two stainless steel electrodes immersible in said fluid.

12. Apparatus according to either of claim 1 or claim 2 wherein said electrode system further comprises an electric current control system for supplying pulses of electricity to the electrodes, said pulses effective to measure said electrical conductance and/or electrical resistance.

13. Apparatus according to either of claim 1 or claim 2 wherein said electrode system comprises electrodes which are not immersed in said fluid.

14. Apparatus according to either of claim 1 or claim 2 wherein said electrode system further comprises a temperature measurement element for measuring the temperature of said fluid.

15. Apparatus according to claim 1 further comprising a radiation source in alignment with said surface to provide radiation including wavelengths less than and equal to 254 nanometers.

16. Apparatus according to claim 1 further comprising a radiation source in alignment with said surface to provide radiation including radiation in the range of from about 160 nanometers to about 200 nanometers.

17. Apparatus according to claim 1 in which an element effective to provide step (d) further comprises a fluid flow control for stopping flow of said irradiated water into said electrode system and for retaining said part of said irradiated water in said electrode system for a third predeterminable time and temperature.

18. Apparatus according to claim 2 in which an element effective to provide step (h) further comprises a fluid flow control for stopping flow of said non-irradiated water into said electrode system and for retaining said non-irradiated water in said electrode system for a fourth predeterminable time and temperature.

19. Apparatus for estimating organic carbon content of water, said apparatus comprising:
an organic carbon oxidation chamber having a fluid inlet conduit and a fluid exit conduit, wherein at least part of said chamber between said inlet and outlet conduits is at least substantially permeable to radiation capable of generating radiation-initiated products of said organic carbon;
said fluid exit conduit is in fluid communication with a measurement system effective to measure one or more of said radiation-initiated products of said organic carbon;
a fluid source to provide a stream of said water to said organic carbon oxidation chamber;
said apparatus further comprising a fluid flow control system comprising a combination of elements to effect seriatim the steps:
(a) flowing said stream seriatim through said fluid inlet conduit, said oxidation chamber, said fluid exit conduit and said measurement system, thereby flushing said conduits, said chamber and said measurement system and at least partly filling said chamber with said water;
(b) stopping flow of said stream, whereby said chamber remains at least partly filled with said water;
(c) irradiating said water in said chamber with said radiation at least through said part of said chamber substantially permeable to said radiation for a first predeterminable time and temperature to generate radiation-initiated products of organic carbon in said water in said chamber, thereby producing irradiated water;
(d) flowing at least part of said irradiated water into said measurement system;
(e) stopping flow of said irradiated water into said measurement system whereby said measurement system retains said part of said irradiated water;
(f) measuring said one or more of said radiation-initiated products of said organic carbon, thereby producing a first measure of said radiation-initiated products;
(g) estimating said organic carbon content at least in part from said first measure, thereby producing an estimate of said organic carbon content;
(h) transmitting by means of electrical signal and/or displaying and/or recording said estimate.

20. Apparatus according to claim 19 for estimating organic carbon content of water, said apparatus further comprising additional fluid flow control elements to effect the following steps seriatim upon demand:
(i) retaining said water from step (b) in said chamber without irradiating said water with said radiation for a second predeterminable time and temperature substantially equivalent to said first predeterminable time and temperature, thereby producing non-irradiated water;
(j) flowing at least part of said non-irradiated water from step (i) into said measurement system;
(k) stopping flow of said non-irradiated water into said measurement system, whereby said measurement system retains said part of said non-irradiated water;
(l) measuring said one or more radiation-initiated products of said organic carbon in said part of said non-irradiated water, thereby producing a second measure of said radiation-initiated products;
(m) estimating said organic carbon content at least in part from said first measure and said second measure, thereby producing an improved estimate of said organic carbon content; and,
(n) transmitting by means of electrical signal and/or displaying and/or recording said improved estimate.

21. In a process for estimating organic carbon content of a stream of water using an organic carbon irradiation chamber having a fluid inlet conduit and a fluid exit conduit, wherein at least part of said chamber between said inlet and outlet conduits is substantially permeable to radiation capable of generating radiation-initiated products of said organic carbon, said fluid exit conduit being in fluid communication with a measurement system to measure one or more of said radiation-initiated products or said organic carbon, the improvement comprising seriatim the following steps:
(a) flowing said stream seriatim through said fluid inlet conduit, said irradiation chamber, said fluid exit conduit, and said measurement system, thereby flushing said conduits, said chamber and said measurement system, and at least partly filling said chamber with said water;
(b) stopping flow of said stream, whereby said chamber remains at least partly filled with said water;
(c) irradiating said water in said chamber with said radiation at least through said part of said chamber substantially permeable to said radiation for a first predeterminable time and temperature to generate radiation-initiated products of organic carbon in said water in said chamber, thereby producing irradiated water;
(d) flowing at least part of said irradiated water into said measurement system;
(e) stopping flow of said irradiated, water into said measurement system, whereby part of said irradiated water is retained in said measurement system;
(f) measuring said one or more of said radiation-initiated products of said organic carbon in said part of said irradiated water, thereby producing a first measure of said radiation-initiated products;

(g) estimating said organic carbon content at least in part from said first measure, thereby producing an estimate of said organic carbon content; and, (h) transmitting by means of electrical signal and/or displaying and/or recording said estimate.

22. A process according to claim 21 further comprising the following additional steps seriatim:

(i) retaining said water from step (b) in said chamber without irradiating said water with said radiation for a second predeterminable time and temperature, thereby producing non-irradiated water;

(j) flowing at least part of said non-irradiated water from step (i) into said measurement system;

(k) stopping flow of said non-irradiated water into said measurement system, whereby part of said irradiated water is retained in said measurement system;

(l) measuring said one or more of said radiation-innitiated products of said organic carbon in said part of said non-irradiated water, thereby producing a second measure of said radiation-initiated products;

(m) estimating said organic carbon content at least in part from said first measure and said second measure, thereby producing an alternative estimate of said organic carbon content; and, (n) transmitting by means of electrical signal and/or displaying and/or recording said alternative estimate.

23. The process of claim 21 further wherein said estimate of said organic carbon content is compared with a predeterminable value of said estimate.

24. The process of claim 21 further comprising a step in which said estimate of said organic carbon content is compared with a predeterminable value of said estimate, and a signal is generated if said estimate is greater than said predeterminable estimate.

25. The process of claim 21 further comprising a step comparing said estimate of said organic carbon content with a predeterminable value of said estimate and generating a signal if said estimate is less than said predeterminable estimate.

26. The process of claim 22 wherein step (h) is omitted.

27. The process of claim 21 wherein step (h) is carried out in conjunction with comparing said estimate of said organic carbon content with a predeterminable value of said estimate, and generating a signal if said estimate is less than said predeterminable value.

28. The process of claim 22 in which steps (g), (h), (m) and (n) comprise a step in which said second measure is subtracted from said first measure to produce a measure difference, and a signal is generated if said measure difference is less than a predeterminable measure difference.

29. Apparatus for estimating the organic carbon content of water, said apparatus comprising:

an organic carbon irradiation chamber having a fluid inlet conduit and a fluid exit conduit, wherein at least part of said chamber is substantially permeable to radiation capable of generating radiation-initiated products of said organic carbon, said fluid exit conduit being in fluid communication with measuring means effective to measure one or more of said products, means to provide a stream of said water, and means effective to provide seriatim the following steps:

(a) flowing said stream seriatim through said inlet conduit, said chamber, said exit conduit and said measuring means, thereby at least partly filling said chamber with said water;

(b) stopping flow of said stream, whereby said chamber remains at least partly filled with said water;

(c) irradiating said water in said chamber with said radiation for a first predeterminable time and temperature effective to produce products of said organic carbon in said water, thereby producing irradiated water;

(d) flowing at least part of said irradiated water into said measuring means;

(e) stopping flow of said irradiated water into said measuring means, whereby said measuring means retains part of said irradiated water (f) effecting a measure of one or more of said products in said measuring means, thereby producing a first measure of said products;

said apparatus further comprising one or more additional means selected from the group consisting of:

A. estimating means for estimating said organic carbon content at least in part from said first measure, thereby producing an estimate of said organic carbon content B. displaying and/or recording means for displaying an estimate of said organic carbon content.

C. first measure comparing means for comparing said first measure with a predeterminable value of said first measure.

D. logic means for estimating said organic carbon content at least in part from said first measure, thereby producing an estimate of said organic carbon content, and for comparing said estimate with a predeterminable value of said estimate E. irradiating means for irradiating said water in said chamber with radiation effective to react said organic carbon substantially to carbon dioxide, carbonic acid and/or bicarbonate, and to predetermine said first predeterminable time and temperature at values sufficient to react said organic carbon substantially to carbon dioxide, carbonic acid and/or bicarbonate as products of said organic carbon in said water.

F. shielding means effective substantially to shield said measuring means from said radiation G. temperature and electrical conductivity and/or electrical resistance detecting means in said measuring means H. temperature and electrical conductivity and/or electrical resistivity detecting means in said measuring means, said detecting means comprising stainless steel electrodes immersible in fluid in said measuring means, I. irradiating means for irradiating said water in said chamber with radiation including wavelengths less than and equal to 254 nanometers, J. irradiating means for irradiating said water in said chamber with radiation including wavelengths in the range of from about 160 nanometers to about 200 nanometers, and, K. stepping means to provide seriatim steps including a step flowing said stream seriatim through said inlet conduit, said chamber, said exit conduit and said measuring means, thereby at least partly filling said chamber with said water; a step stopping flow of said stream whereby said chamber remains at least partly filled with said water; a step retaining water from said last mentioned step in said chamber for a second predeterminable time and temperature in the absence of irradiating said water with said radiation; a step flowing at least part of water retained in said chamber in said last mentioned step into said measuring means and stopping flow of said water, whereby said measuring means retains part of said water; a step effecting a measure of said one or more of said products in water retained in said measuring means in said last mentioned step.

\* \* \* \* \*